United States Patent [19]

Matsumori et al.

[11] Patent Number: 4,722,894

[45] Date of Patent: Feb. 2, 1988

[54] METHOD FOR THE DETERMINATION OF CERULOPLASMIN ACTIVITY

[75] Inventors: Shigeru Matsumori; Yoshiaki Shimizu, both of Shizuoka; Toshio Tatano, Numazu, all of Japan

[73] Assignee: Kyowa Medex Co., Ltd., Tokyo, Japan

[21] Appl. No.: 697,749

[22] Filed: Feb. 4, 1985

[30] Foreign Application Priority Data

Feb. 3, 1984 [JP] Japan ................... 59-16950

[51] Int. Cl.⁴ .................. C12Q 1/26; C12Q 1/28; C12Q 1/00
[52] U.S. Cl. ...................... 435/25; 435/4; 435/28; 435/810
[58] Field of Search ............ 435/4, 25, 28, 810

[56] References Cited

U.S. PATENT DOCUMENTS

| | | | |
|---|---|---|---|
| 3,042,496 | 7/1962 | Fancher et al. | 435/25 |
| 3,072,539 | 1/1963 | Fancher et al. | 435/25 |
| 4,098,574 | 7/1978 | Dappen | 435/25 |
| 4,228,240 | 10/1980 | Dawson et al. | 435/28 |
| 4,554,249 | 11/1985 | Kosaka et al. | 435/25 |
| 4,587,220 | 5/1986 | Mayambala-Mwanika | 435/28 |

FOREIGN PATENT DOCUMENTS

| | | | |
|---|---|---|---|
| 127179 | 12/1984 | European Pat. Off. | 435/25 |
| 3314308 | 10/1984 | Fed. Rep. of Germany | 435/28 |
| 57-68797 | 4/1982 | Japan | 435/25 |

OTHER PUBLICATIONS

Wynn et al, Biochem., 23(2):241–247, Jan. 17, 1984.

*Primary Examiner*—Esther M. Kepplinger
*Attorney, Agent, or Firm*—Antonelli, Terry & Wands

[57] ABSTRACT

The present invention provides a method for the determination of ceruloplasmin activity, wherein a member selected from the group consisting of (a) ferrocene or derivatives thereof (b) metallocene and (c) chelate metal containing iron or copper is reacted with a chromogen in the presence of ceruloplasmin to form colored material which is determined photometrically, as well as a reagent suitable therefor.

6 Claims, No Drawings

METHOD FOR THE DETERMINATION OF CERULOPLASMIN ACTIVITY

BACKGROUND OF THE INVENTION

The present invention relates to a method for the determination of ceruloplasmin activity and a reagent suitable therefor.

Ceruloplasmin, which is a glycoprotein enzyme containing copper, is one of plasma protein and is present in an $\alpha_2$-globulin fraction in a concentration of 0.5% on the basis of total serum. It has an activity to oxidize divalent iron into trivalent iron.

The determination of ceruloplasmin activity is useful for diagnosis of liver cirrhosis, chronic hepatitis, liver failure, Wilson's desease, etc.

Heretofore, as to the assay of ceruloplasmin, single radial diffusion method for the immunologic quantitation of proteins (SRID method) and colorimetric method using diamine oxidase are known. There are problems of time-consuming reaction (usually, more than 24 hours) and inaccuracy of results in the former method. The latter is a simpler method than the former, but the reaction rate is slow and it takes 15–30 minutes to complete the reaction. The blank reagent is colored during reaction because the reagent is unstable and therefor it cannot be applied to the usual automatic assay instrument.

SUMMARY OF THE INVENTION

In accordance with the present invention, ceruloplasmin activity in a sample can be determined by reacting (a) ferrocene or derivatives thereof (b) metallocene or (c) chelate metal containing iron or copper with a chromogen in the presence of ceruloplasmin to form a pigment and measuring the change in the absorption of the reaction solution.

DETAILED DESCRIPTION OF THE INVENTION

As the derivatives of ferrocene used in the present invention, $\alpha$-hydroxyferrocene, benzoylferrocene, 1,1-ferrocene-dicarboxylic acid, acetylferrocene, N,N-dimethylaminomethylferrocene, etc. are exemplified. As the metallocene, cobaltocene, nickelocene, zirconocene, titanocene, etc. and as the chelate metal, ferrous diethyl-dithiocarbamic acid DDC-Fe), ferrous acetylacetonate, EDTA-Fe, copper acetylacetonate, etc. may be used in a concentration of 10 $\mu$M - 1 mM.

As the chromogen, 4-aminoantipyrine (4AA)-phenol system, 4AA-N-ethyl-N-(3-methylphenyl)-N'-acetylethylenediamine (EMAE) system, N,N-dimethyl-P-phenylenediamine (DPD), methylcarbamoyl-3,7-dimethylamine-10H-phenothiazin (MCDP), Bis[3-bis(4-chlorophenyl)methyl-4-dimethylaminophenyl] amine (BCMA), etc. may be used in a concentration of 10 $\mu$M - 1 mM.

The reaction is carried out in a buffer solution such as acetate, citrate at a pH of 4–6, preferably 5.

Suitable surfactant such as Triton X-100, polyoxyethylenelaurylether, sodium laurylsulfate, polyoxyethylenealkyl, etc. may be used to increase solubility of an additive or to take out turbidity due to serum containing fat in high concentration.

The absorption change of the reaction solution at the maximum absorption of the formed pigment, usually 600–800 nm is measured after one to 15 minutes pass since the reaction starts.

Standard curve for the relation between ceruloplasmin activity and absorption rate is measured in advance and ceruloplasmin activity can be obtained using the same.

The reaction rate was measured in the following method when MCDP was used as chromogen.

One mg of compounds indicated in Table 1 and 1.65 mg of MCDP were added to 100 ml of acetate buffer to prepare a reagent solution. To a cell was poured 3 ml of the reagent solution and the solution was incubated at 37° C. 30 $\mu$l of serum was added to the solution. The absorption change of the reaction solution at 663 nm was measured for one minute, after two minutes passed since the reaction started. The results are shown in Table 1. $\Delta E$ shows the absorption change.

TABLE 1

|  | $\Delta E \times 10^3$/min |
|---|---|
| Control | 1 |
| Ferrocene | 63 |
| $\alpha$-Hydroxyferrocene | 61 |
| Benzoylferrocene | 12 |
| 1,1-Ferrocene-dicarboxylic acid | 60 |
| Acetylferrocene | 30 |
| N,N—Dimethylaminomethylferrocene | 45 |
| Cobaltnocene | 3 |
| Titanocene | 3 |
| Zirconocene | 2 |
| Nickelocene | 2 |
| Ferrous diethyl-dithio-carbamic acid | 24 |
| Ferrous acetylacetonate | 3 |
| EDTA-Fe | 2 |
| Copper acetylacetonate | 3 |

The similar procedures were repeated using 20 mg of 4AA-EMAE, DPD or MCDP each to obtain the results shown in Table 2.

TABLE 2

| Chromogen | No Addition of ferrocene | Addition of ferrocene |
|---|---|---|
| 4AA-EMAE | 1 | 7 |
| D P D | 3 | 7 |
| MCDP | 1 | 63 |

The results obtained according to the present invention is not influenced by substances in serum because the reaction speed is very high and ceruloplasmin activity can be measured with accuracy for a short period.

Certain specific embodiments of the invention are illustrated by the following representative example.

EXAMPLE 1

0.2M-acetate buffer: 11.3 ml
0.2M-sodium acetate solution: 38.7 ml
Triton X-100: 0.1 g
Water: 50 ml To 100 ml of a solution (pH 5.3) having the above-mentioned composition were added 1 mg of ferrocene and 1.65 mg of MCDP to prepare a reagent solution. Then, 3 ml of the reagent solution was poured into a cell and incubated at 37° C. for 5 minutes. To the solution was added 30 $\mu$l of serum and the absorption change of reaction solution at 663 nm was measured for one minutes, after two minutes passed since the reaction started. The results are shown in Table 3.

The same procedures as described above were repeated except that 10 mg of N,N-dimethylaminomethylferrocene (Test No. 2), 10 mg of titanocene (Test No. 3), 10 mg of nickelocene (Test No. 4), 7.5 mg of DDC-Fe (Test No. 5) or 10 mg of acetylacetone copper (Test No. 6) instead of ferrocene or 10 mg of N,N-dimethylaminomethylferrocene instead of ferrocene and 12.3 mg of oxalate of DPD instead of HCDP (Test No. 7) were used to obtain the results in Table 3.

TABLE 3

| Test No. | Sample 1 | | | Sample 2 | | |
|---|---|---|---|---|---|---|
| | A | U/ml | S | A | U/ml | S |
| 1 | 63 | 79 | 30.2 | 110 | 138 | 52.8 |
| 2 | 45 | 56 | 30.2 | 78 | 98 | 52.3 |
| 3 | 3 | 3.7 | 30.0 | 5 | 6.3 | 50.0 |
| 4 | 2 | 2.5 | 28.0 | 4 | 5.0 | 56.0 |
| 5 | 24 | 30 | 31.2 | 41 | 51 | 53.3 |
| 6 | 3 | 3.8 | 30.0 | 5 | 6.3 | 50.0 |
| 7 | 15 | 19 | 30.0 | 26 | 33 | 52.0 |

A: $\Delta E/min \times 10^3$
S: Content of ceruloplasmin (mg/dl)
U: International unit

What is claimed is:

1. A method for determining ceruloplasmin activity in a serum sample which comprises reacting a chromogen with a member selected from the group consisting of (a) ferrocene or derivative thereof, (b) metallocene and (c) chelate metal containing iron or copper in the presence of ceruloplasmin to form a pigment and measuring the change in the absorption of the reaction solution at visible ray region; said chromogen being selected from the group consisting of 4-aminoantipyrine (4AA)-phenol system, 4AA-N-ethyl-N-(3-methylphenyl)-N'-acetybethylene-diamine (EMAE) system, N,N-dimethyl-P-phenylenediamine (DPD), methylcarbamoyl-3,7-dimethylamine-10H-phenothiazin (MCDP) and Bis[3-bis(4-chlorophenyl)methyl-4-dimethylaminophenyl]amine (BCMA).

2. A method according to claim 1, wherein said ferrocene derivative is selected from the group consisting of α-hydroxyferrocene, benzoylferrocene, 1,1-ferrocenedicarboxylic acid, acetylferrocene and N,N-dimethylaminomethylferrocene.

3. A method according to claim 1, wherein said metallocene is selected from the group consisting of cobaltocene, nickelocene, zirconocene, and titanocene.

4. A method according to claim 1, wherein said chelate metal is selected from the group consisting of ferrous diethyl-dithiocarbamic acid, ferrous acetylacetonate, EDTA-FE and copper acetylacetonate.

5. A method according to claim 1, wherein said reaction is carried out in a buffer solution at a pH of 4–6.

6. A method according to claim 1, wherein said measurement is carried out at maximum wavelength of the chromogen.

* * * * *